| (12) | United States Patent | (10) Patent No.: | US 10,188,401 B2 |
|---|---|---|---|
| | Zwirkoski et al. | (45) Date of Patent: | Jan. 29, 2019 |

(54) SURGICAL DEVICES FOR INTERVENTIONAL ORTHOPEDIC SURGICAL APPLICATIONS AND PROSTHETIC TRIAL DEVICES AND METHODS OF MAKING THE SAME

(71) Applicant: ZJ, LLC, Whitmore Lake, MI (US)

(72) Inventors: Paul A. Zwirkoski, Hamburg Township, MI (US); Joseph T. Adams, Howell, MI (US)

(73) Assignee: ZJ, LLC, Whitmore Lake, MI (US)

( * ) Notice: Subject to any disclaimer, the term of this patent is extended or adjusted under 35 U.S.C. 154(b) by 314 days.

(21) Appl. No.: 14/901,916

(22) PCT Filed: Jul. 1, 2014

(86) PCT No.: PCT/US2014/045126
§ 371 (c)(1),
(2) Date: Dec. 29, 2015

(87) PCT Pub. No.: WO2015/002993
PCT Pub. Date: Jan. 8, 2015

(65) Prior Publication Data
US 2016/0374691 A1    Dec. 29, 2016

Related U.S. Application Data

(60) Provisional application No. 61/957,430, filed on Jul. 1, 2013.

(51) Int. Cl.
*A61B 17/15* (2006.01)
*A61F 2/46* (2006.01)
(Continued)

(52) U.S. Cl.
CPC .......... *A61B 17/155* (2013.01); *A61F 2/4684* (2013.01); *A61B 2017/00526* (2013.01);
(Continued)

(58) Field of Classification Search
CPC ......... A61B 17/15; A61B 17/155; A61F 2/46; A61F 2/4684
See application file for complete search history.

(56) References Cited

U.S. PATENT DOCUMENTS 6,575,980 B1    6/2003  Robie et al.
8,377,141 B2 *  2/2013  McMinn .................. A61F 2/38

FOREIGN PATENT DOCUMENTS

WO    WO-2011/063123 A2    5/2011
WO    WO 2011063123 A2 *   5/2011 ......... A61B 17/1764
(Continued)

OTHER PUBLICATIONS

International Search Report and Written Opinion for Application No. PCT/US2014/045126, dated Jan. 20, 2015.

*Primary Examiner* — Christopher Beccia
(74) *Attorney, Agent, or Firm* — Marshall, Gerstein & Borun LLP

(57) ABSTRACT

A posterior stabilized cruciate notch femoral cut guide shaped to fit over the distal end of a femur and including various cut guides to prepare the femur for a knee implant and methods for its use. Also described is a method for manufacturing the posterior stabilized cruciate notch femoral cut guide and various other cut guides and trialing instruments.

3 Claims, 25 Drawing Sheets

(51) Int. Cl.
   *A61F 2/38*   (2006.01)
   *A61F 2/30*   (2006.01)
   *A61B 17/00*  (2006.01)

(52) U.S. Cl.
   CPC ... *A61B 2017/00707* (2013.01); *A61F 2/3094* (2013.01); *A61F 2/3859* (2013.01)

(56) References Cited

FOREIGN PATENT DOCUMENTS

| WO | WO 2012024323 A2 * | 8/2011 | ............. A61B 17/15 |
| WO | WO-2012/024323 A2 | 2/2012 | |
| WO | WO-2012/156806 A1 | 11/2012 | |

\* cited by examiner

701

Prior Art

Prior Art

Prior Art

SURGICAL DEVICES FOR INTERVENTIONAL ORTHOPEDIC SURGICAL APPLICATIONS AND PROSTHETIC TRIAL DEVICES AND METHODS OF MAKING THE SAME The priority benefit of U.S. Application No. 61/957,430, filed on Jul. 1, 2013, is claimed and incorporated by reference in its entirety.

FIELD OF DISCLOSURE

The present application generally concerns surgical preparatory guides intended to assist surgeons in making the necessary preliminary bone cuts for the targeting or treatment of specific locations during an operation, specifically a total knee reconstruction (TKR), methods of manufacturing these guides, and methods for the use of these guides.

BACKGROUND OF THE DISCLOSURE

Currently, traditional cut guide designs and instruments are bulky, one-piece components that are expensive to produce. Such traditional cut guides are heavy, cumbersome, non-adjustable in rotation, and have permanently captured cutting slots, which can complicate the surgeon's efforts to properly prepare accurate surgical cuts needed for a successful TKR. Examples of such traditional cut guides are illustrated by the traditional posterior stabilized cruciate notch femoral cut guide 200 shown in FIGS. 11 and 12, and the traditional distal femoral cut guide 3000 depicted in FIG. 25. There is a need for lighter, more efficient and less costly cut guides as disclosed herein. Disclosed herein are instruments, and their methods to manufacture and use, that provide the surgeon with the ability to achieve all of his/her precise preparatory cuts, angular and rotational adjustments, functional checks, and trial confirmation with better designed and less expensive instrumentation.

Femoral trials are instruments that resemble the implanted femoral component and are critical for surgeons to assess and confirm proper restoration of critical outcomes and performance parameters including joint mechanics, range of motion, and soft tissue balance. Like the traditional cut guides, traditional femoral trials are a complex geometry and when provided with traditional methods are expensive and time consuming to produce. The described femoral trial is considerably less expensive to produce, while still satisfying the demanding surgical performance requirements that such an instrument must meet during the procedure.

SUMMARY

Broadly described here are surgical cut guides that contain holes, slots, and/or apertures created from single or multiple layers of flat metal template cut and/or template cut and bent or stacked, three dimensionally formed and/or assembled together in a given arrangement, permitting for the guided usage of surgical instruments such as drills, saws, grinders, punches, broaches, scopes, needles, portals, etc. More specifically described are embodiments of femoral cut guides that allow for lightweight instruments with improved intra-operative adjustability and improved functional trial confirmation which surgeons can utilize when preparing the femur. Also described are methods of manufacturing these various surgical instruments that are considerably less expensive to manufacture than traditional surgical instruments.

Disclosed herein is a femoral cut guide, specifically a posterior stabilized cruciate notch femoral cut guide. This cut guide consists of a single bent flat sheet of stainless steel and provides captured and non-captured cutting slots as a traditional femoral cut guide would, but in a lightweight form that is easier to use for the surgeon.

Also disclosed is a femoral cut guide, specifically a four-in-one cut guide that allows the surgeon to perform an anterior cut, anterior chamfer cut, posterior cut, and posterior chamfer cut to the femur. The four-in-one cut guide consists of multiple flat template cut plates of stainless steel that are bent, arranged and nested together in a manner establishing four distinct cutting slots. The individual bent components may be assembled by various techniques. For example, all components can be permanently fixated to each other by weldments or rivets, or alternatively, the anterior and posterior modular plates could be mechanically attached via torque until failure connections for one time removal of these plates for use of an open face cut guide, or alternatively, all components can be mechanically fixated temporarily by means of, screws, lugs, rivets, or quick connections, allowing for disassembly and reassembly of the cut guide. All of the various connection methods are readily known and appreciated by those skilled in the art. In one embodiment, the four-in-one cut guide may also consist of a pivoting pin plate that allows for the surgeon to intra-operatively adjust the angle of the axis orientation of the cut guide. This affords the surgeon the opportunity to appropriately size the anterior-posterior dimensional balance while allowing internal and external rotational adjustment prior to performing all four-in-one cuts.

Further disclosed is a femoral trial for performance trailing the reconstructed knee to verify whether the reconstructed knee meets surgical parameters. The femoral trial simulates the to be implanted femoral prosthesis, and satisfies surgical needs in terms of assessment and confirmation of joint mechanics, range of motion, and soft tissue balance. The femoral trial consists of a bent stainless steel plate stacked with plastic overmolded three dimensional articulating surfaces which are strong enough to withstand forces produced by a slap hammer during operative usage, while also providing accurate anatomic geometries of the femur.

Finally described is a method of manufacturing the previously described surgical cut guides and instruments that is far less expensive than the method currently employed for producing similar traditional surgical instruments. The defined method will utilize flat sheets of metal, such as various flat stock metals, that are bent to their desired shape and form, and accordingly stacked, layered, and nested into their preferred embodiment. This method produces instruments that are lighter in weight, more intra-operatively adaptable, and inexpensive, that accomplish the same surgical requirements as traditional surgical cut guides.

BRIEF DESCRIPTION OF SEVERAL VIEWS OF THE DRAWINGS

Embodiments and variations are now described by way of example with reference to the accompanying drawings.

DETAILED DESCRIPTION

Described herein are preparatory surgical cutting guides and trials for usage during an operation, specifically a posterior stabilized cruciate notch femoral cut guide, a four-in-one cut guide, and a femoral trial used in various total knee reconstructions (TKR) and numerous other orthopedic procedures. Also detailed are methods of manufacturing these various instruments.

Figure 1:
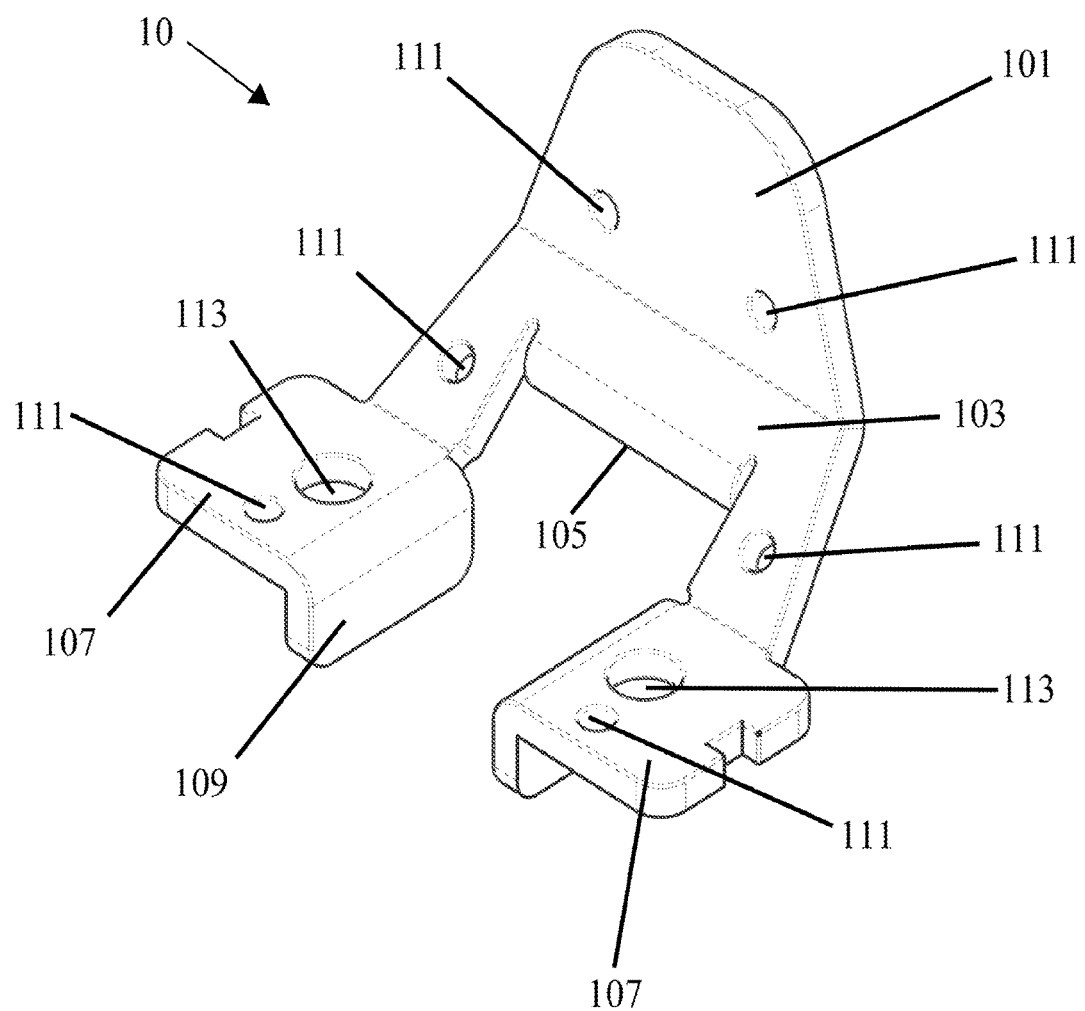
FIG. 1 shows a rear isometric view of a posterior stabilized cruciate notch femoral cut guide.

FIG. 1 shows a preferred embodiment of a posterior stabilized cruciate notch femoral cut guide 10 consisting of a first end having an anterior face section 101, a body having an anterior chamfered face 103 transitioning into an anterior cutting face 105, and two flat distal sections 107 forming a second end of the posterior stabilized cruciate notch femoral cut guide 10, with each of the two flat distal sections 107 transitioning into medial and lateral cutting faces 109 facing an interior of the device. The posterior stabilized cruciate notch femoral cut guide 10 is shaped to prepare and duplicate the mating faces of a TKR, more specifically the TKR cruciate notch of the femoral component. Included as part of the device are fastener openings 111 for the delivery of fixation fasteners such as threaded pins to secure the posterior stabilized cruciate notch femoral cut guide 10 once it is placed in the proper location on a femur, with the two flat distal sections 107 pressed against a distal portion of the femur bone and the anterior face section 101 pressed against an anterior portion of the femur bone. Also included are two drill guide openings 113 on the two flat distal sections 107. These two drill guide openings 113 are used to prepare holes in the distal portion of the femur for eventual placement of femoral implant lugs for improved implant fixation.

Figure 2:
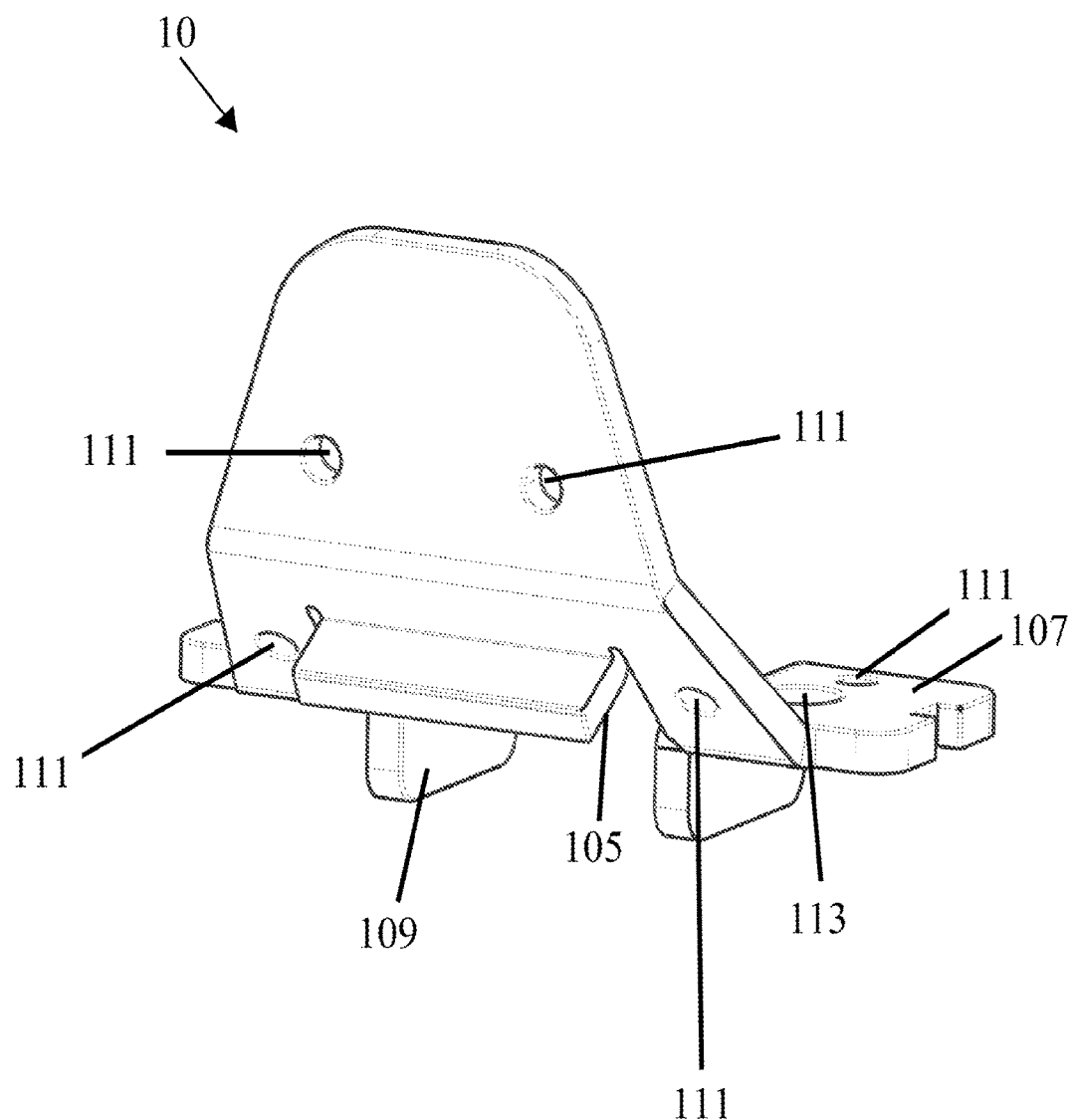
FIG. 2 shows a front isometric view of the posterior stabilized cruciate notch femoral cut guide.
Figure 3:
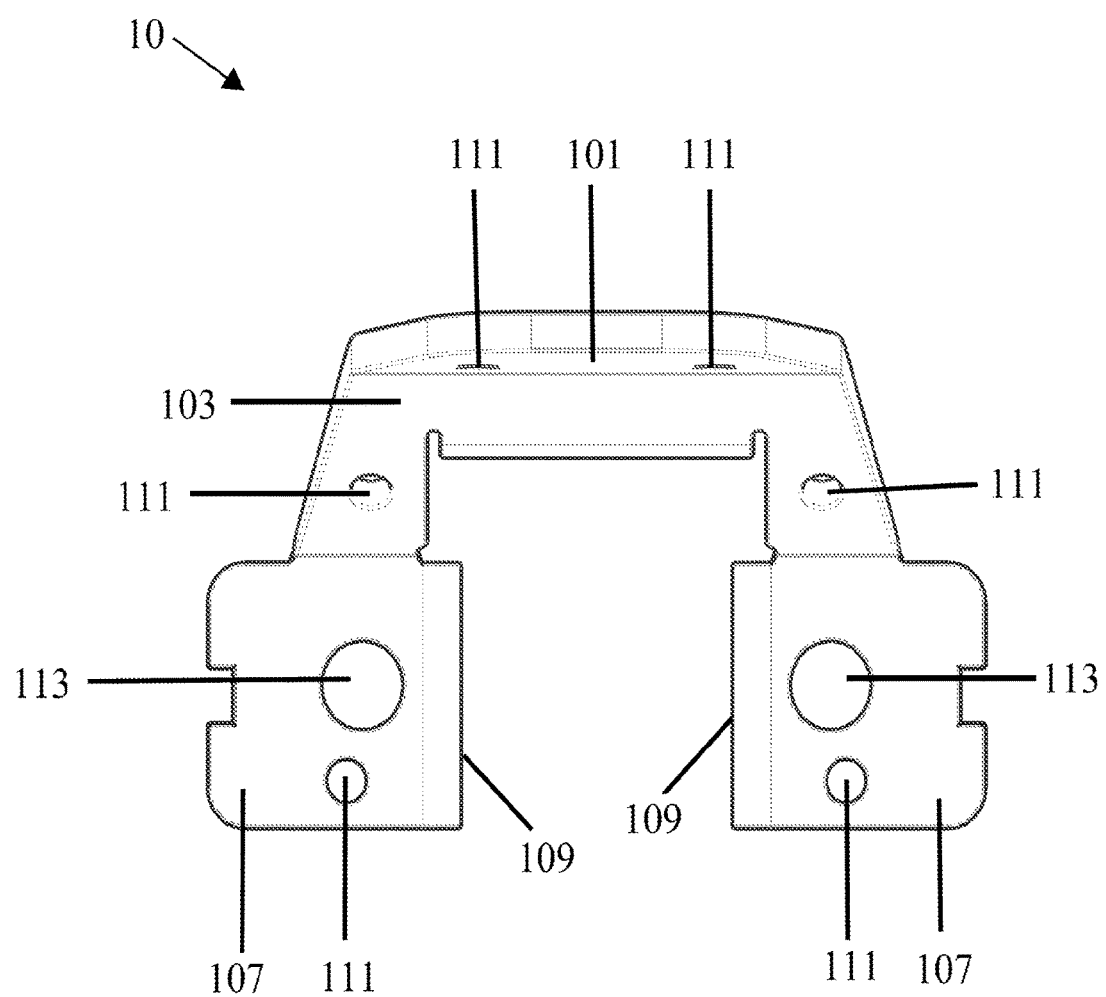
FIG. 3 shows a top view of the posterior stabilized cruciate notch femoral cut guide.
Figure 4:
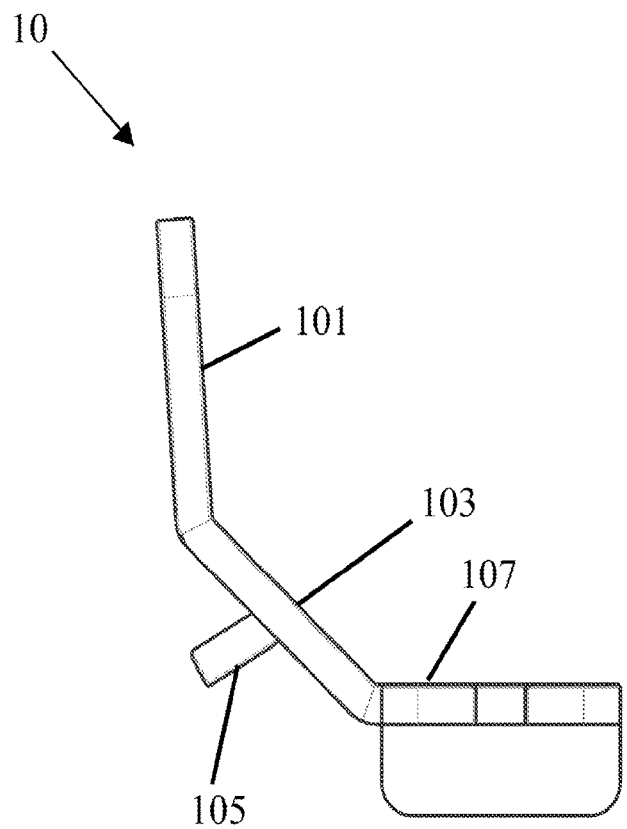
FIG. 4 shows a side view of the posterior stabilized cruciate notch femoral cut guide.
Figure 5:
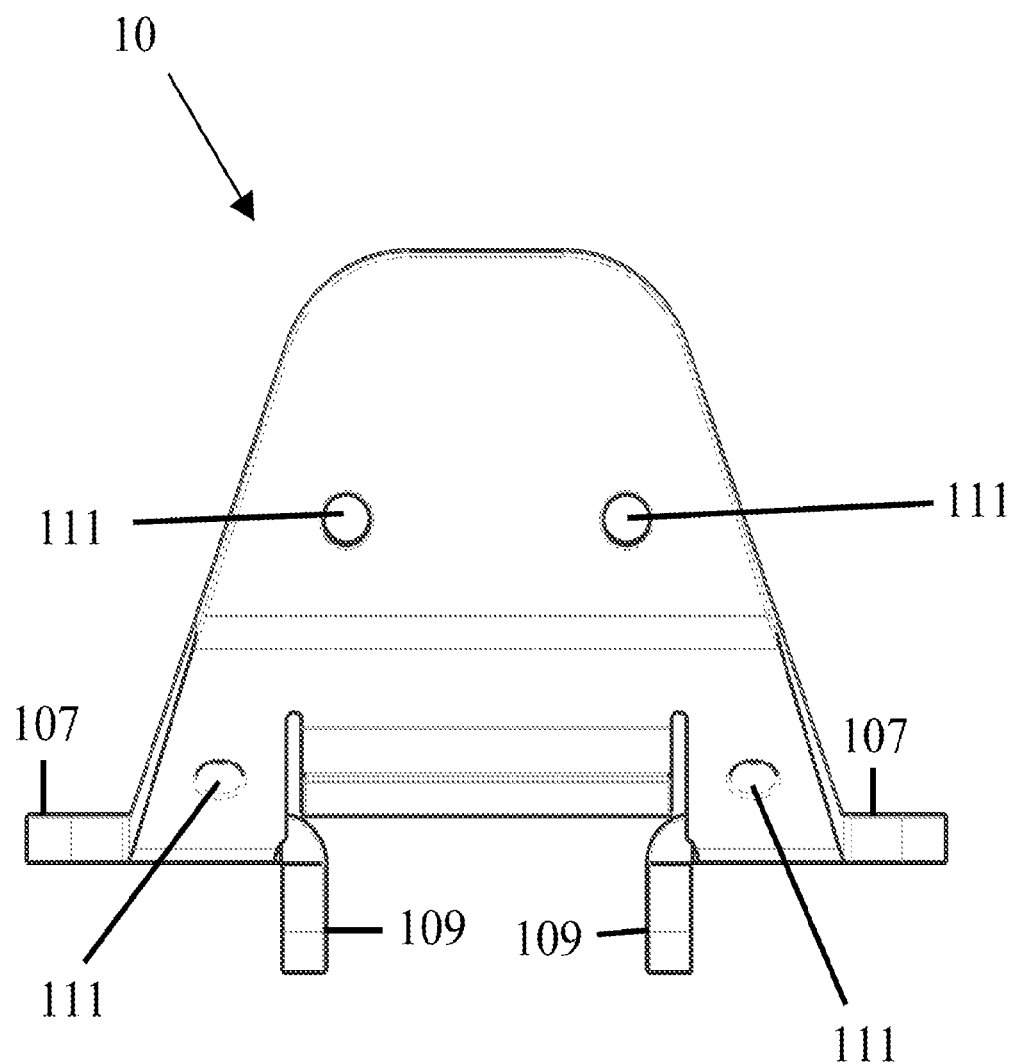
FIG. 5 shows a front view of the posterior stabilized cruciate notch femoral cut guide.
Figure 6:
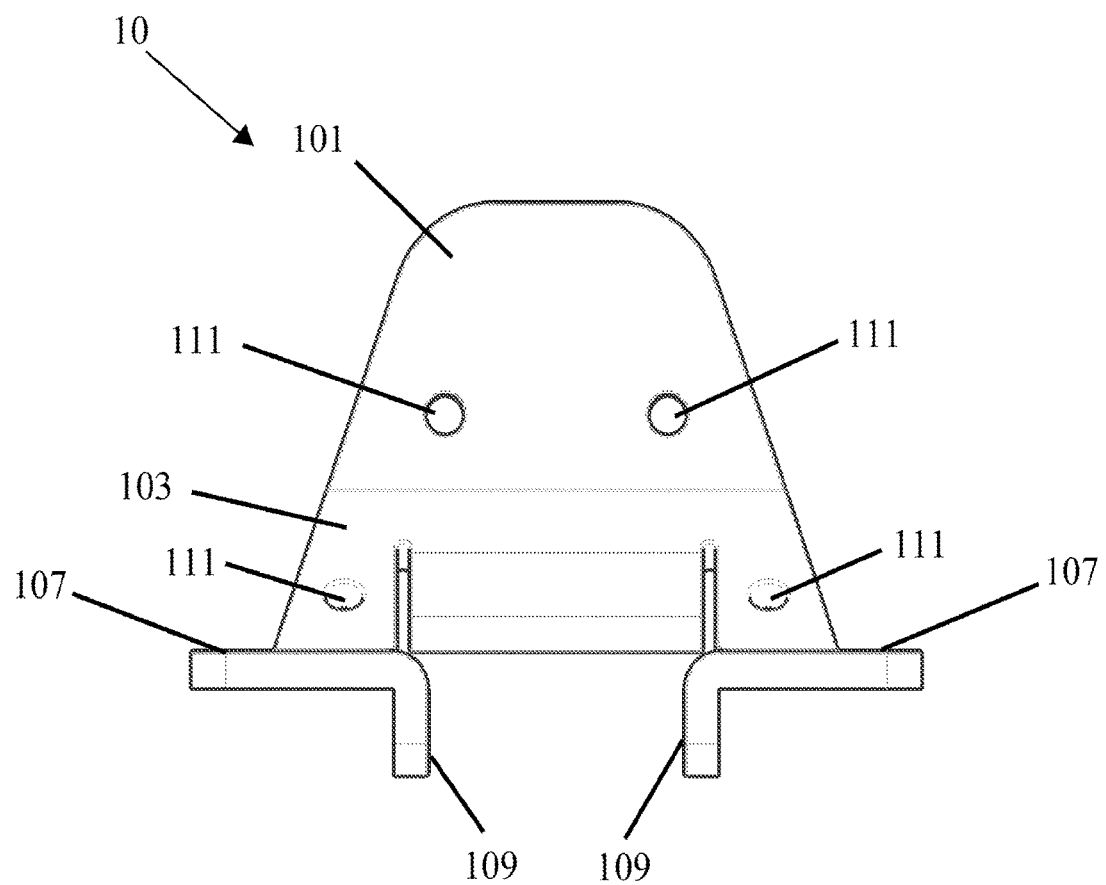
FIG. 6 shows a rear view of the posterior stabilized cruciate notch femoral cut guide.

FIGS. 2-6 show various perspectives of the posterior stabilized cruciate notch femoral cut guide 10. FIG. 2 shows an isometric view of the device, FIG. 3 shows a top view, FIG. 4 shows a side view, FIG. 5 shows a front view and FIG. 6 shows a rear view.

Figure 7:
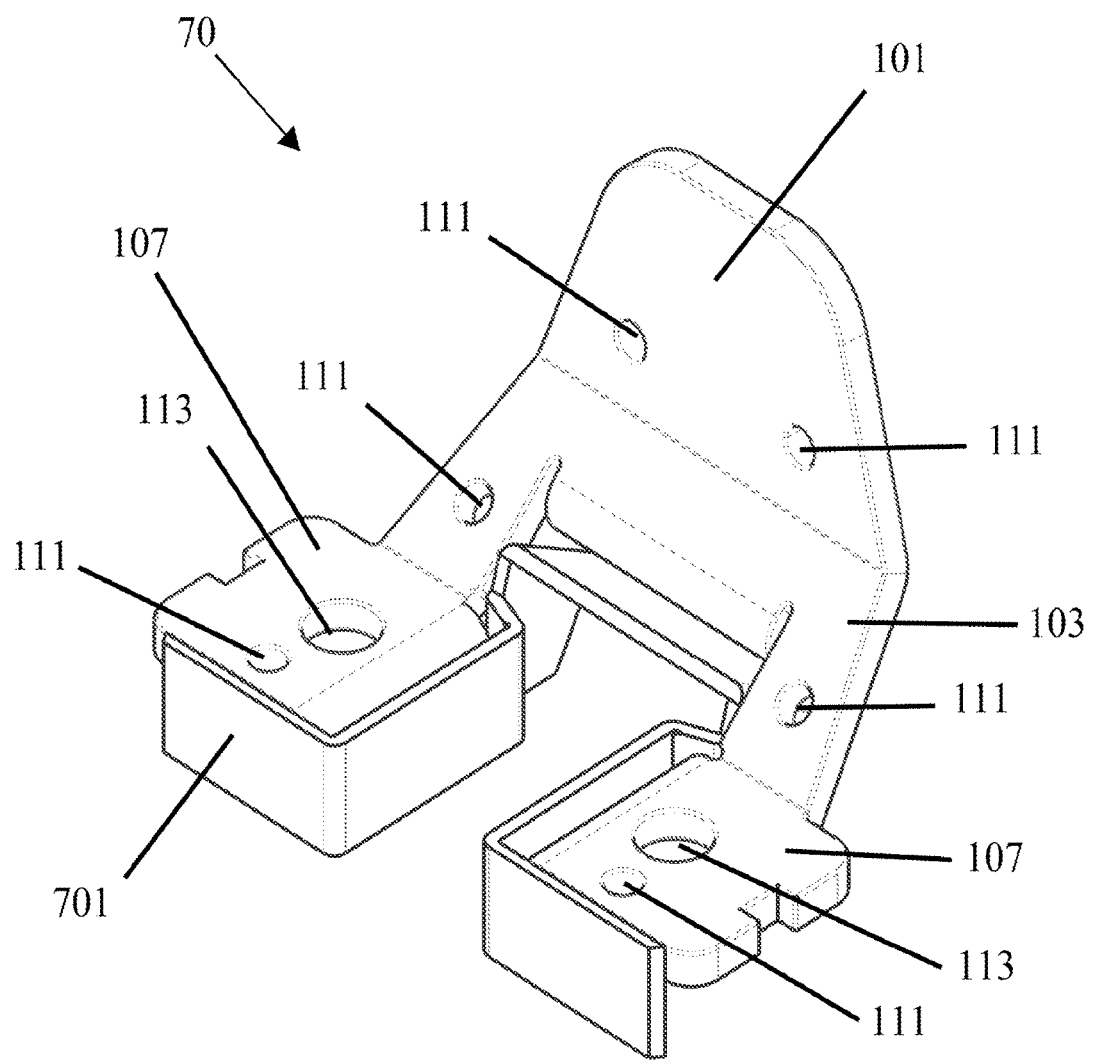
FIG. 7 shows a rear isometric view of the posterior stabilized cruciate notch femoral cut guide with an attached cutting guide insert.
Figure 8:
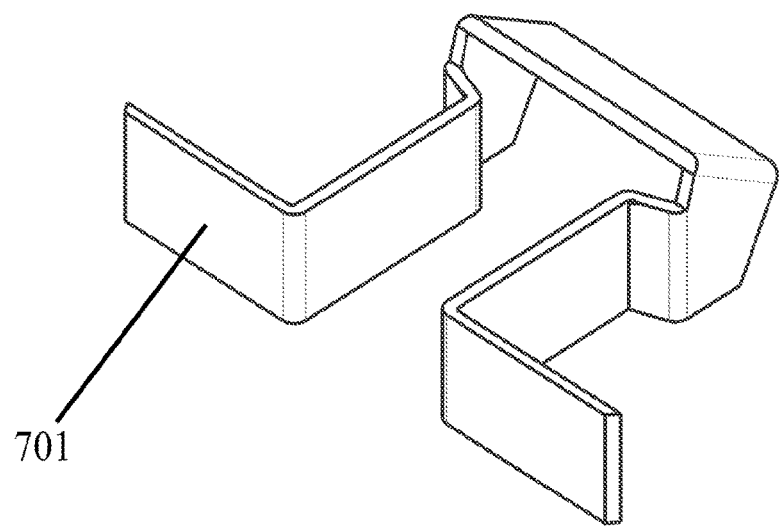
FIG. 8 shows an isometric view of only the cutting guide insert.
Figure 9:
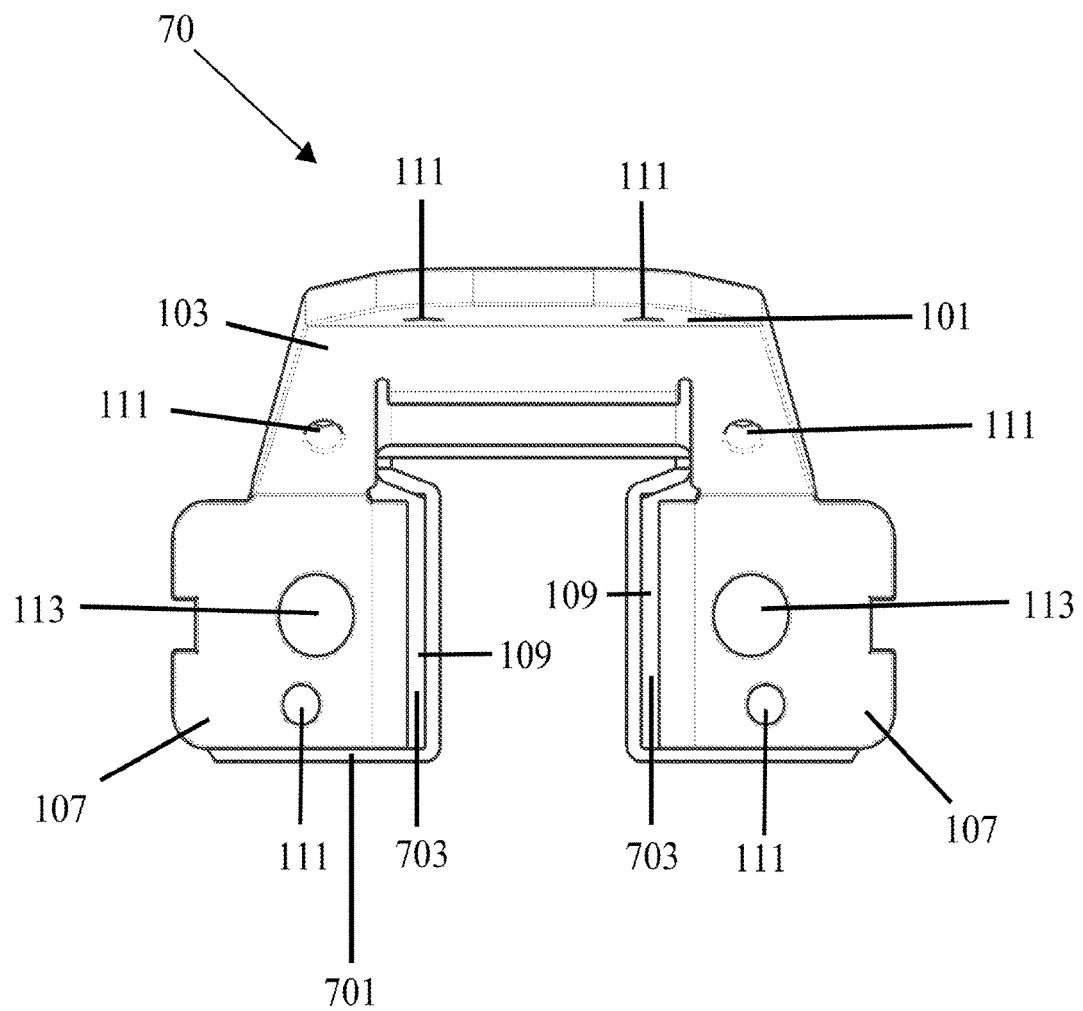
FIG. 9 shows a top view of the posterior stabilized cruciate notch femoral cut guide with the attached cutting guide insert.

In one embodiment, the posterior stabilized cruciate notch femoral cut guide may be a captured posterior stabilized cruciate notch femoral cut guide 70 with an attached cutting guide insert 701, as shown in FIG. 7. The cutting guide insert 701 allows for captured cutting slots 703, shown in FIG. 9, into which the user can insert a cutting instrument which will assist in angular constraint while cutting. This aspect of the captured posterior stabilized cruciate notch femoral cut guide 70 reduces the risk of misalignment of the cutting instrument relative to the cutting guide face during the femoral cutting process. FIG. 8 shows only the cutting guide insert component and FIG. 9 shows a top view of the captured posterior stabilized cruciate notch femoral cut guide 70 with a cutting guide insert 701 and resulting captured cutting slots 703.

Figure 10:
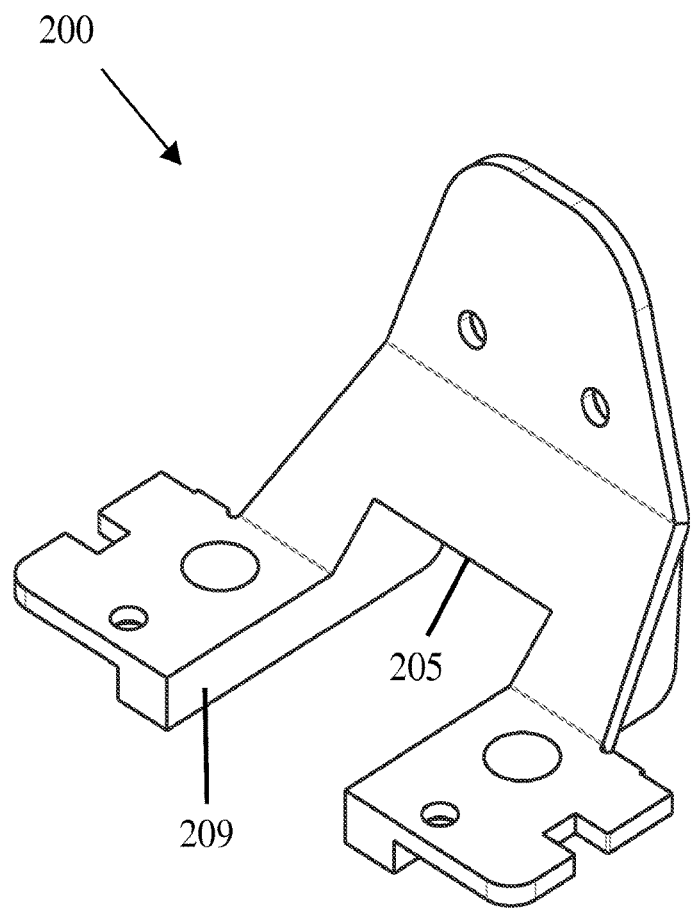
FIG. 10 shows a rear isometric view of a traditional posterior stabilized cruciate notch femoral cut guide.
Figure 11:
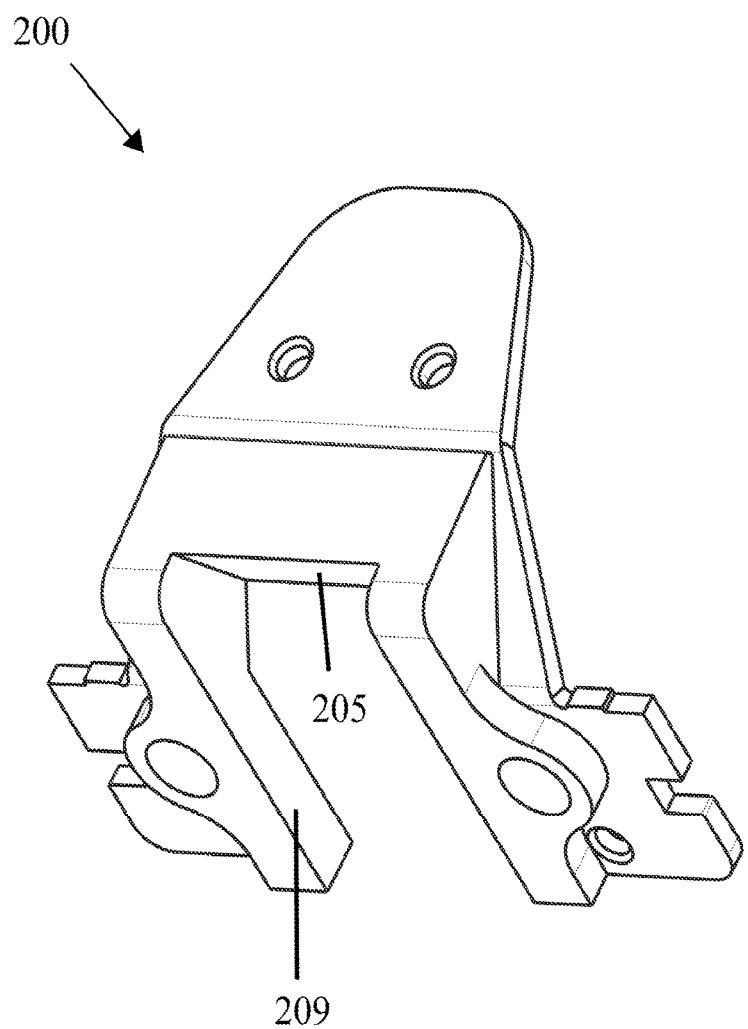
FIG. 11 shows a front isometric view of the traditional posterior stabilized cruciate notch femoral cut guide.

FIG. 10 shows a traditional posterior stabilized cruciate notch femoral cut guide 200 with the medial and lateral cut guide faces 209 extending to the anterior cutting face 205. FIG. 11 shows an alternative iso view of a traditional posterior stabilized cruciate notch femoral cut guide 200.

The method for use of the posterior stabilized cruciate notch femoral cut guide 10 would be to prepare the femur for a posterior stabilized knee implant by positioning the posterior stabilized cruciate notch femoral cut guide 10 at the distal end of the femur and adjusting it to its desired medial lateral position for cutting the bone. Once placed, the posterior stabilized cruciate notch femoral cut guide 10 is secured in place through the placement of fasteners such as pins through two or more of the fastener openings 111. Once secured, the surgeon can cut the desired portion of the femur, utilizing the cutting instrument guided by the anterior cutting face 105 and the medial and lateral cutting faces 109 of the posterior stabilized cruciate notch femoral cut guide 10. After the cutting is complete, the surgeon can create the holes for the implant fixation posts in the femur by means of the drill guide openings 113, remove the cut guide fasteners, and remove the posterior stabilized cruciate notch femoral cut guide 10.

Also described is a method for manufacturing that allows the posterior stabilized cruciate notch femoral cut guide 10 to be cut from one flat sheet metal material, such as stainless steel, and bent to form the desired finished shape as shown in the figures. In the preferred method the posterior stabilized cruciate notch femoral cut guide 10 would be cut out of the flat stock metal material and the fastener openings 111 would be created in the posterior stabilized cruciate notch femoral cut guide 10 prior to bending. The cutting operation may employ laser cutting, punching, die cutting, stamping or any other suitable method for cutting metal. The posterior stabilized cruciate notch femoral cut guide 10 would then be bent along two parallel bending lines to form the anterior face section 101, the anterior chamfered face 103, and the two flat distal sections 107. The two flat distal sections 107 would each contain a slot to aid in the visual view of proper placement of the implant. The anterior cutting face 105, and medial and lateral cutting faces 109 would then be bent, and the drill guide openings 113 would be created. The anterior cutting face 105 may be formed by bending an interior portion of the body of the posterior stabilized cruciate notch femoral cut guide 10. Upon completion of the bending processes, the posterior stabilized cruciate notch femoral cut guide 10 may be heat treated to impart the posterior stabilized cruciate notch femoral cut guide 10 with a desired hardness. Subsequently, the posterior stabilized cruciate notch femoral cut guide may be subjected to a surface finishing operation such as tumbling and/or blasting. In one embodiment, a small extra piece of steel would be left on the outside of the two flat distal sections 107 prior to bending to grip the posterior stabilized cruciate notch femoral cut guide 10 for bending to prevent defects on the portion of the posterior stabilized cruciate notch cut guide 10 that would be the finished product with or without this extra material. The method allows for the manufacture of a finished posterior stabilized cruciate notch femoral cut guide 10 that is lighter, more efficient, and far less expensive than traditional femoral cut guides.

In an alternative embodiment, the posterior stabilized cruciate notch femoral cut guide 10 might be made from a lighter material such as aluminum. After the posterior stabilized cruciate notch femoral cut guide 10 is completed, a surface treatment could be placed on the posterior stabilized cruciate notch femoral cut guide 10 to prevent wear or undesired movement during the cutting process. Many materials could be utilized for coating the posterior stabilized cruciate notch femoral cut guide 10 for surface treatment however, such as a hard plastic material, which could then be coated to prevent wear and small particles from being released as a result of the cutting instruments employed by the users such as surgeons.

It will be appreciated by persons skilled in the art that numerous variations and/or modifications may be made to the described posterior stabilized cruciate notch femoral cut guide 10 and methods as specifically shown here without departing from the spirit or scope of that broader disclosure. The various examples are, therefore, are to be considered in all respects as illustrative and not as limiting.

Additionally described is a four-in-one cut guide that allows the surgeon to execute the following cuts to the femur: anterior cut, anterior chamfer cut, posterior chamfer cut and posterior cut. This cut guide is comprised of numerous flat forms of material that are bent, arranged, and constructed in a manner that produces captured cutting slots for each of the previously described femoral bone cuts. This embodiment also consists of anterior and posterior modular plates that are permanently attached to their respective modular bases by various means such as, but are not limited to, rivets, weldments, or threaded fasteners allowing for captured cutting slots only. Alternatively, another embodiment consists of anterior and posterior plates as well as other components that are temporarily attached to each other and by various means such as, but are not limited to, threaded fasteners, quick connects, etc. This would allow for the four-in-one cut guide to be disassembled and reassembled when desired. The cut guide also has a permanently situated fixation pin plate, which prevents rotation of the cut guide when it is attached to the femur.

Additionally disclosed is an alternate embodiment of the four-in-one cut guide that consists of nonpermanent, mechanically detachable, modular anterior and posterior plates that give the surgeon the ability to utilize either a captured cutting slot or an open face cutting surface when performing the anterior cut and posterior cut to the femur. The anterior and posterior modular plates are attached to their respective modular bases via torque until failure screw mechanism that permits the irreversible conversion of the captured anterior and posterior cutting slots into open face cutting surfaces. The mechanism securing each modular plate to their respective modular base has a given torque failure point. If the user applies a torque greater than said failure point, the attachment mechanism will fail accordingly, allowing for the removal of the selected modular plate. The detachable modular plates are independent of each other so that one modular plate may be removed without removing the other.

Furthermore, described is an embodiment of the four-in-one cut guide that allows for the adjustment of the internal and external rotation of the axis of orientation of the cut guide, which improves the biomechanics of component articulation through the range of motion. The pin plate will not be permanently fixated; instead, the cut guide has the ability to swivel about central pivot point and fixation pins of the pin plate, allowing for slight rotation of the cut guide and alterations to the internal and external axis orientation. This provides the surgeon with the opportunity to alter the angle at which he or she will cut the femur when needed. The described design allows for the cut guide to be aligned appropriately with the boney prominences of the femur to achieve better soft tissue balance during the course of extension and flexion throughout the full range of motion.

Figure 12:
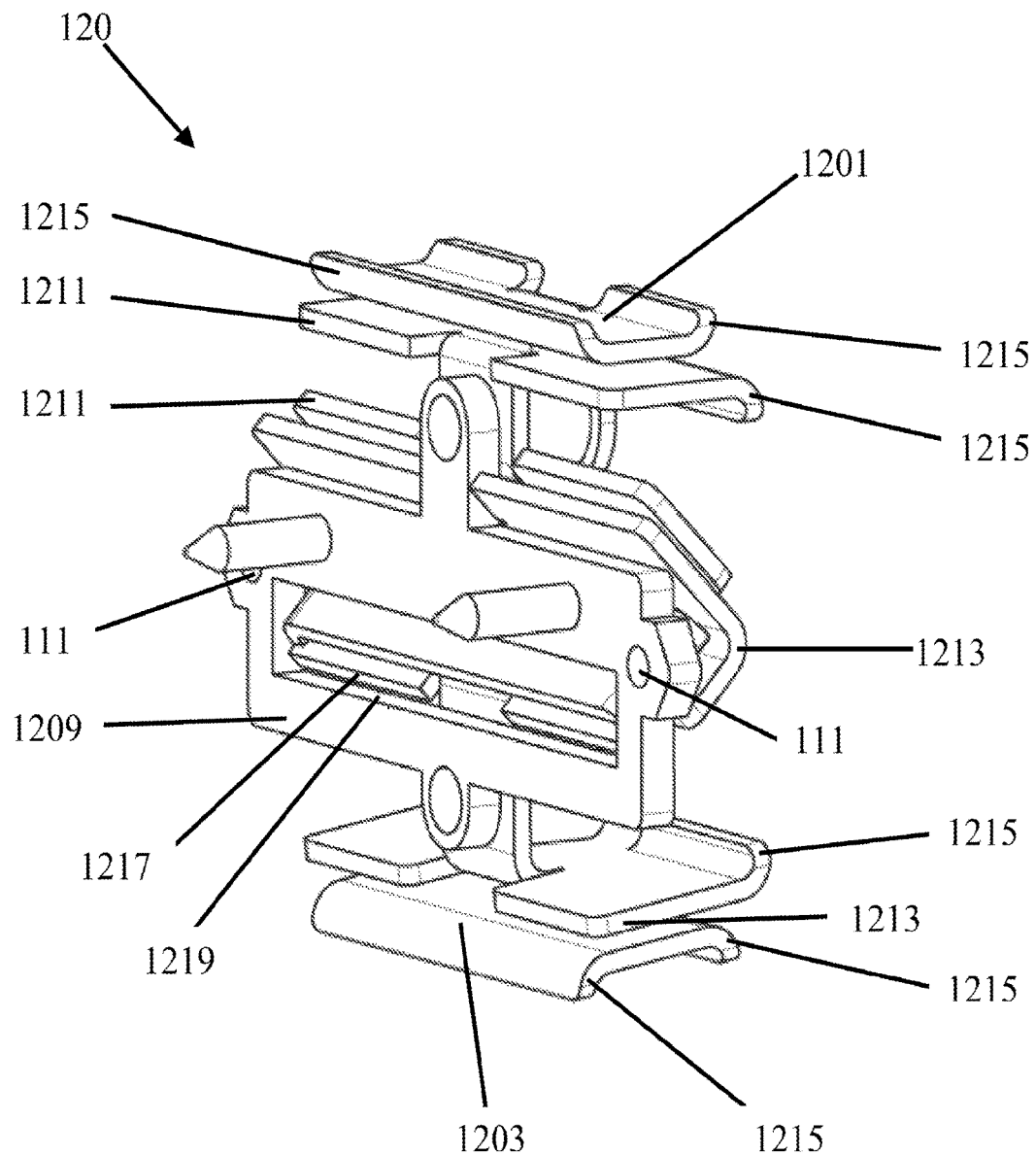
FIG. 12 shows an isometric view of a four-in-one cut guide with mechanically attached anterior and posterior modular slot capture plates.

FIG. 12 shows the embodiment of the four-in-one cut guide 120 with anterior modular plate 1201 and posterior modular plate 1203 attached by means of screw bosses 1205 and socket head cap screws 1207. Excluding the attached anterior modular plate 1201, posterior modular plate 1203, and socket head cap screws 1207, the cut guide is manufactured from three separate flat forms that are bent, stacked and assembled into the desired final shape and form. The resulting layers include pin plate 1209, anterior frame component 1211, and posterior frame component 1213. This embodiment utilizes a mating male tab 1217 within posterior frame component 1213 locking and stiffening the assembly when mated with the female slot 1219 within anterior frame component 1211 and pin plate 1209. As illustrated in FIG. 12, bone fasteners having pointed ends may extend from a bone engaging surface of the pin plate 1209 for securing the four-in-one cut guide 120 to a distal end of the femur bone.

Figure 13:
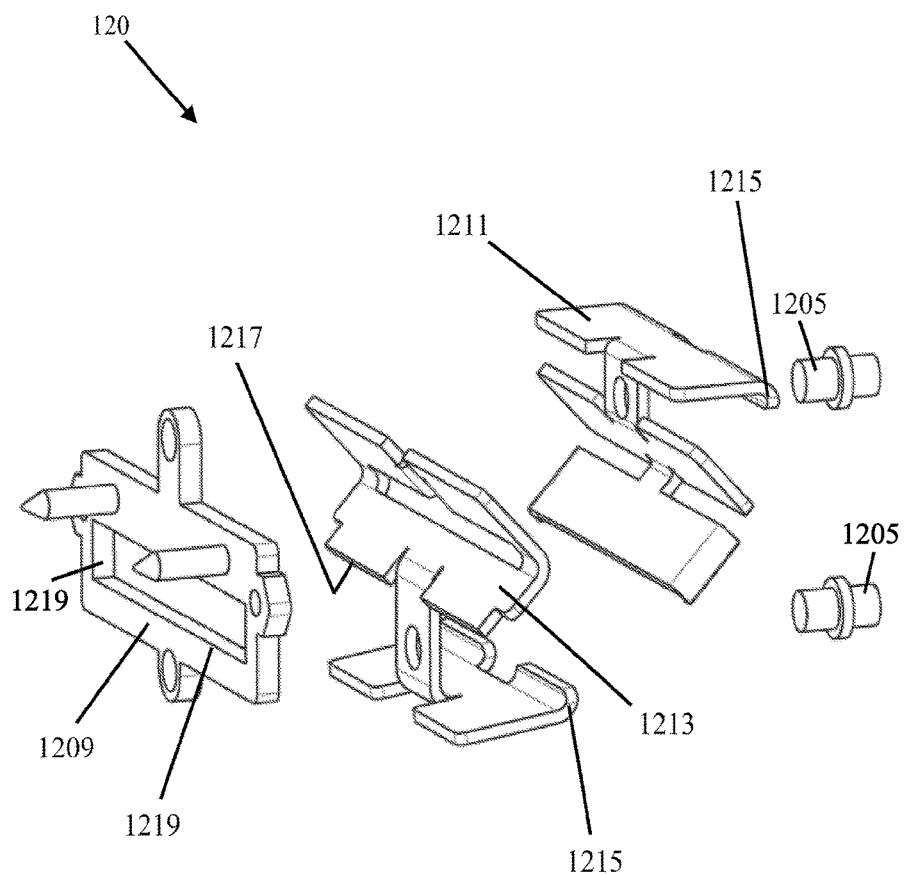
FIG. 13 shows an exploded assembly view of the pin plate, anterior frame component, posterior frame component, and screw bosses of the four-in-one cut guide.

In FIG. 13, select components of four-in-one cut guide 120 are seen in an exploded view. Pin plate 1209, anterior frame component 1211, posterior frame component 1213, and screw bosses 1205 can be seen isolated from each other in their proper stacking order. Excluded and not shown are anterior modular plate 1201, posterior modular plate 1203, and socket head cap screws 1207.

Figure 14:
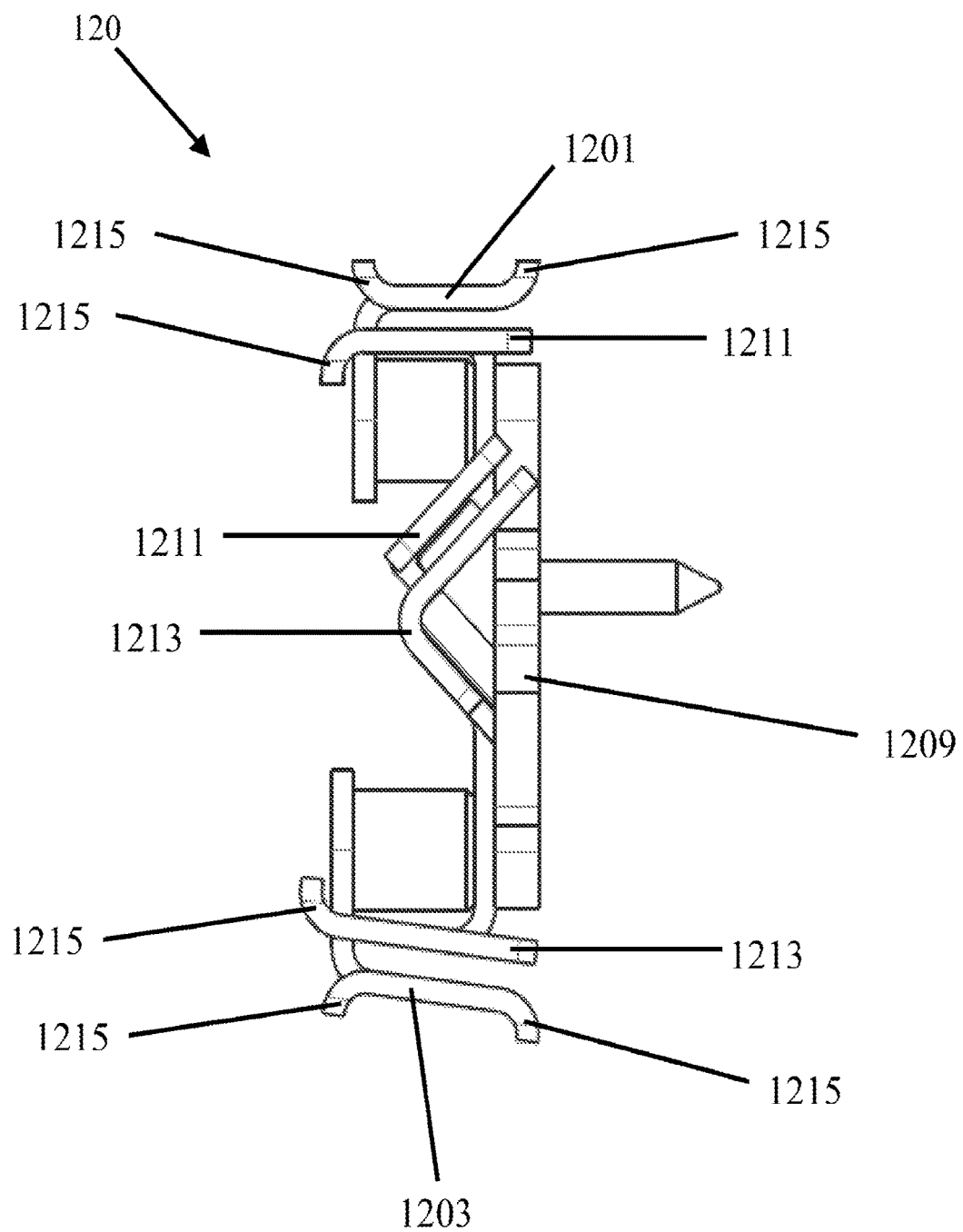
FIG. 14 shows a side view of the four-in-one cut guide with a mechanically attached modular anterior slot capture plate and a mechanically attached modular posterior slot capture plate.
Figure 15:
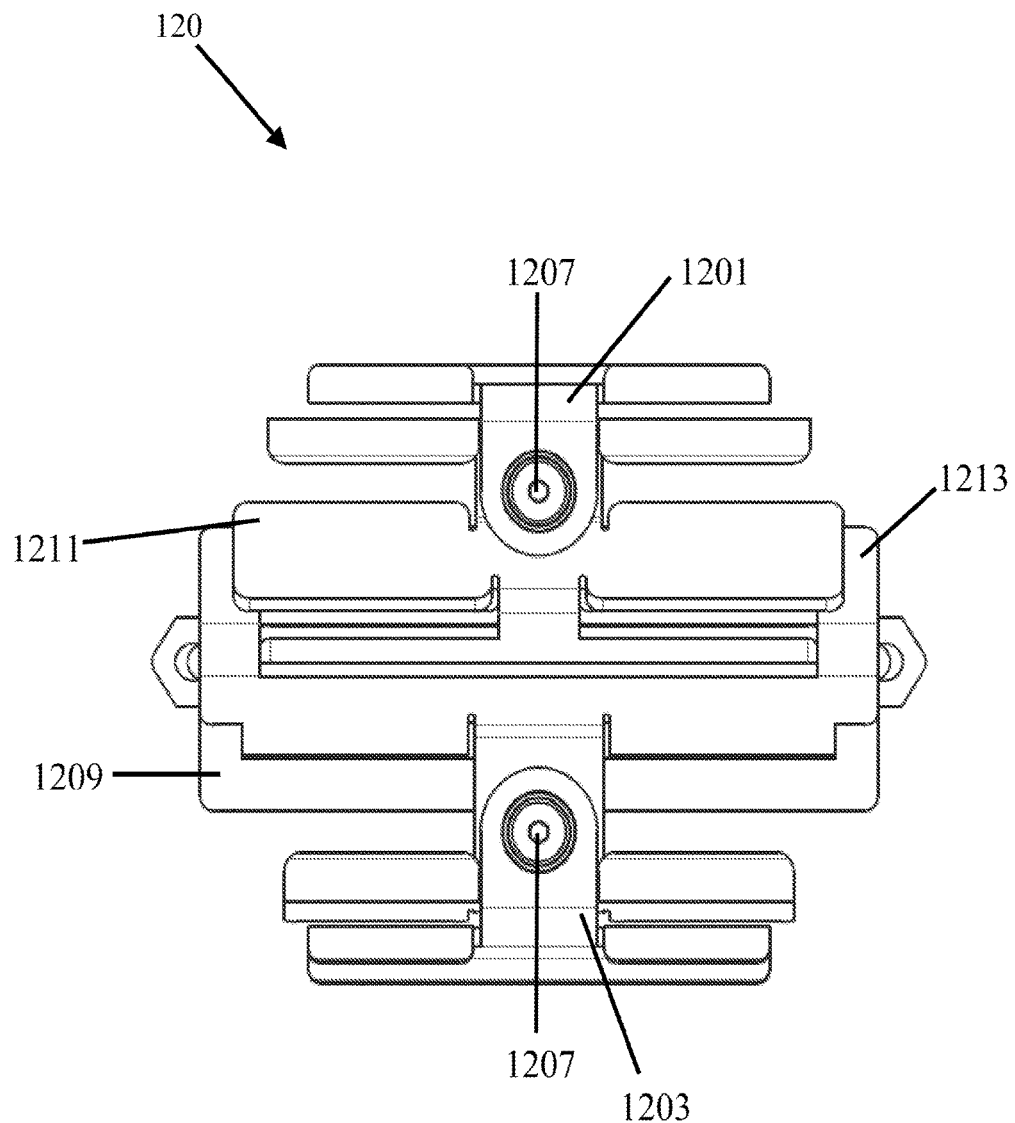
FIG. 15 shows a front view of the four-in-one cut guide with the mechanically attached modular anterior slot capture plate and the mechanically attached modular posterior slot capture plate.

FIGS. 14 and 15 show different perspectives of the four-in-one cut guide 120 with anterior modular plate 1201 and posterior modular plate 1203 attached. FIG. 14 portrays a side view, while FIG. 15 shows a top view.

Figure 16:
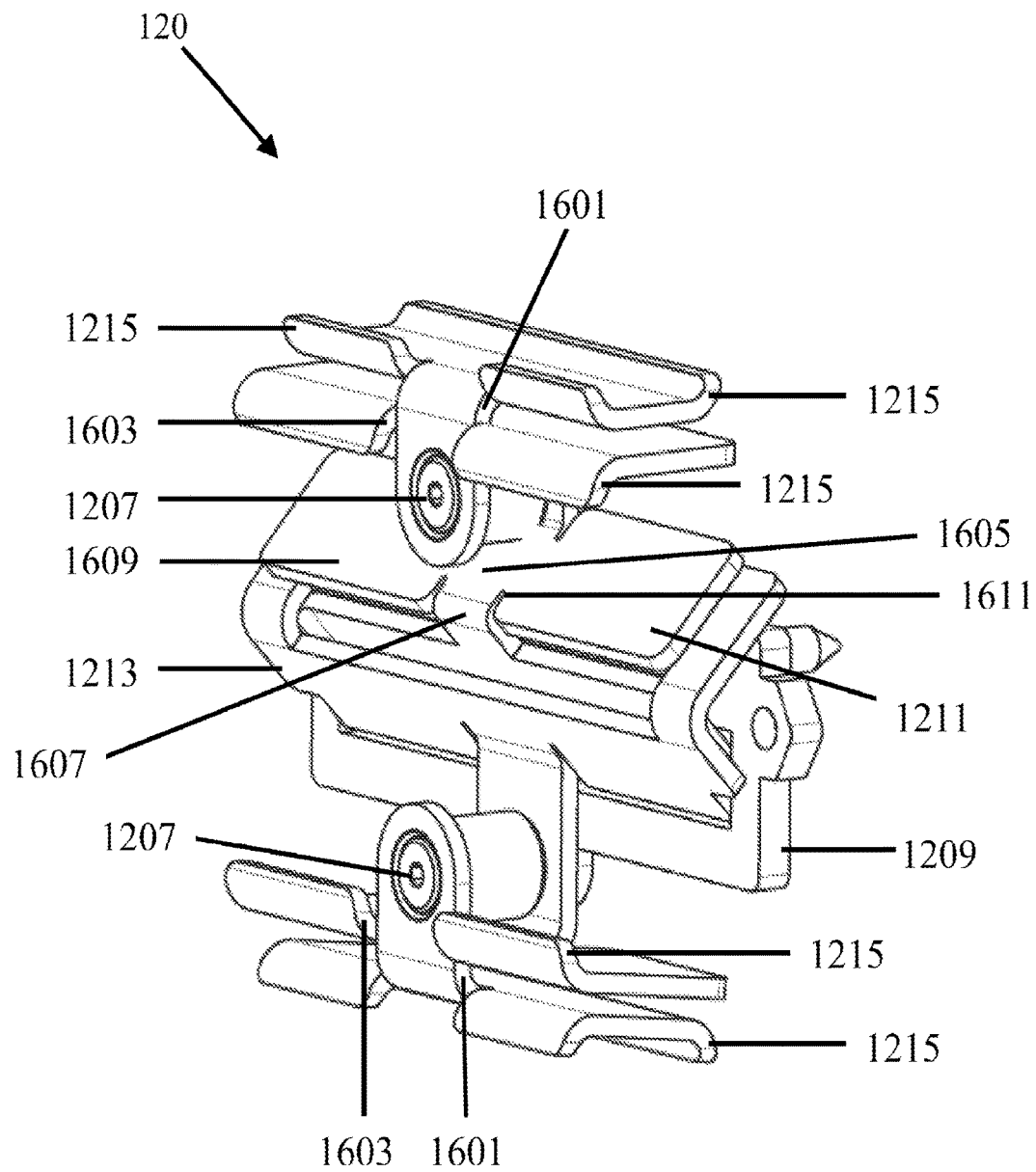
FIG. 16 shows an isometric view of the four-in-one cut guide with both the anterior modular slot capture plate and the posterior modular slot capture plate in place.

FIG. 16 shows an isometric view of the four-in-one cut guide 120 with both the anterior modular plate 1201 and posterior modular plate 1203 in place. Anterior modular plate 1201 and posterior plate 1203 provide captured slots for angular control of the cutting instrument. FIG. 16 also shows a critical modular tab 1601 mating into either an anterior or posterior frame component slot 1603. These features control the anterior modular plate 1201 and posterior modular plate 1203 angular orientation and constrain the modular plates once the various alternative connections have been completed. This design affords greater rigidity and accuracy to the completed assembly. This design allows the connection components to be turned items without anti-rotation features therefore they are simpler and cheaper connection components to manufacture. Another advantageous feature of the various bent components is the planar surface 1605 adjacent to the bent tab 1607 which provides a larger flat surface area 1609 and thereby improves cutting instrument support and control.

Figure 17:
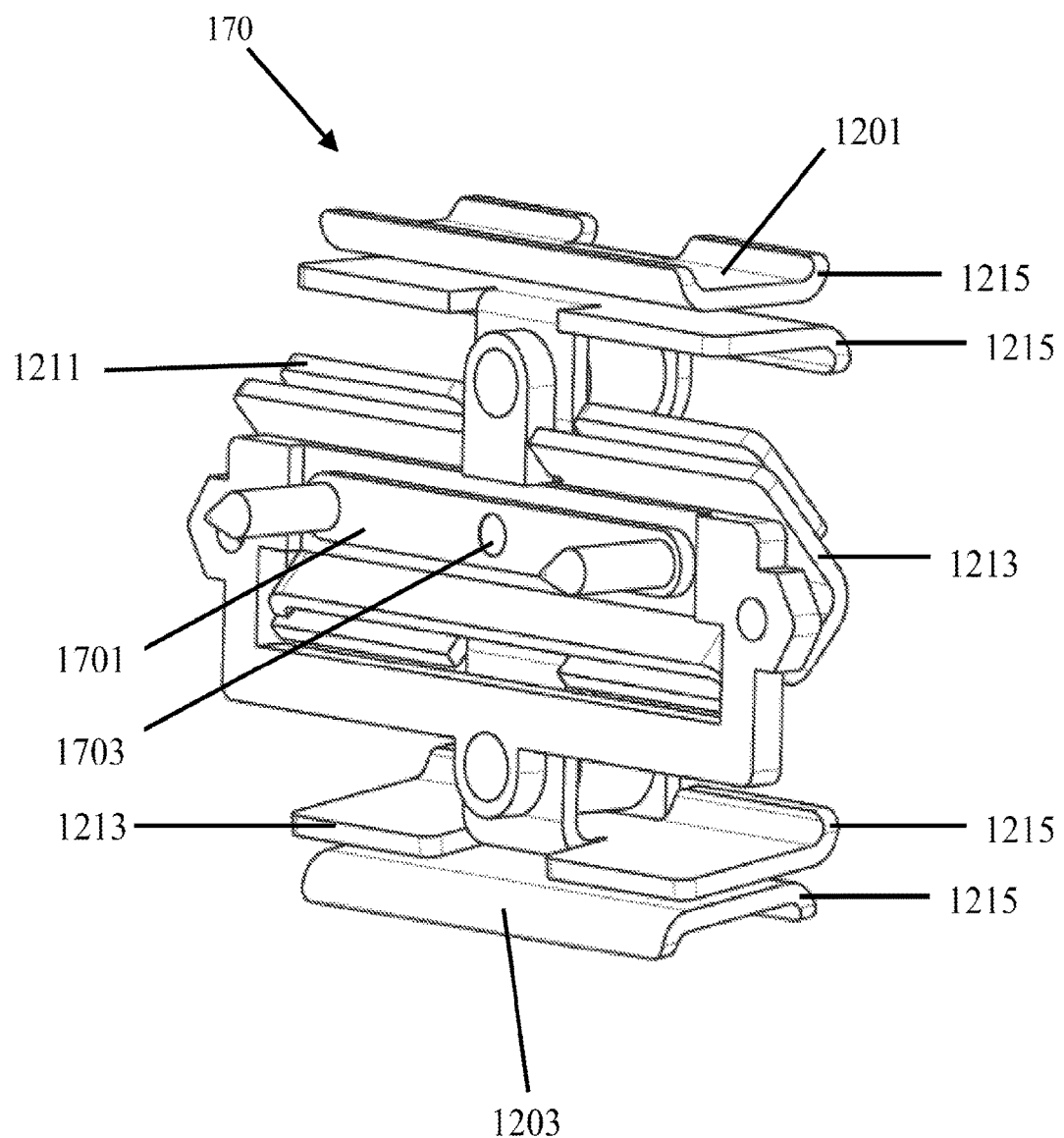
FIG. 17 shows an isometric view of an alternative embodiment of the four-in-one cut guide having a pivoting pin plate allowing for rotational movement about an axis of the four-in-one cut guide.
Figure 18:
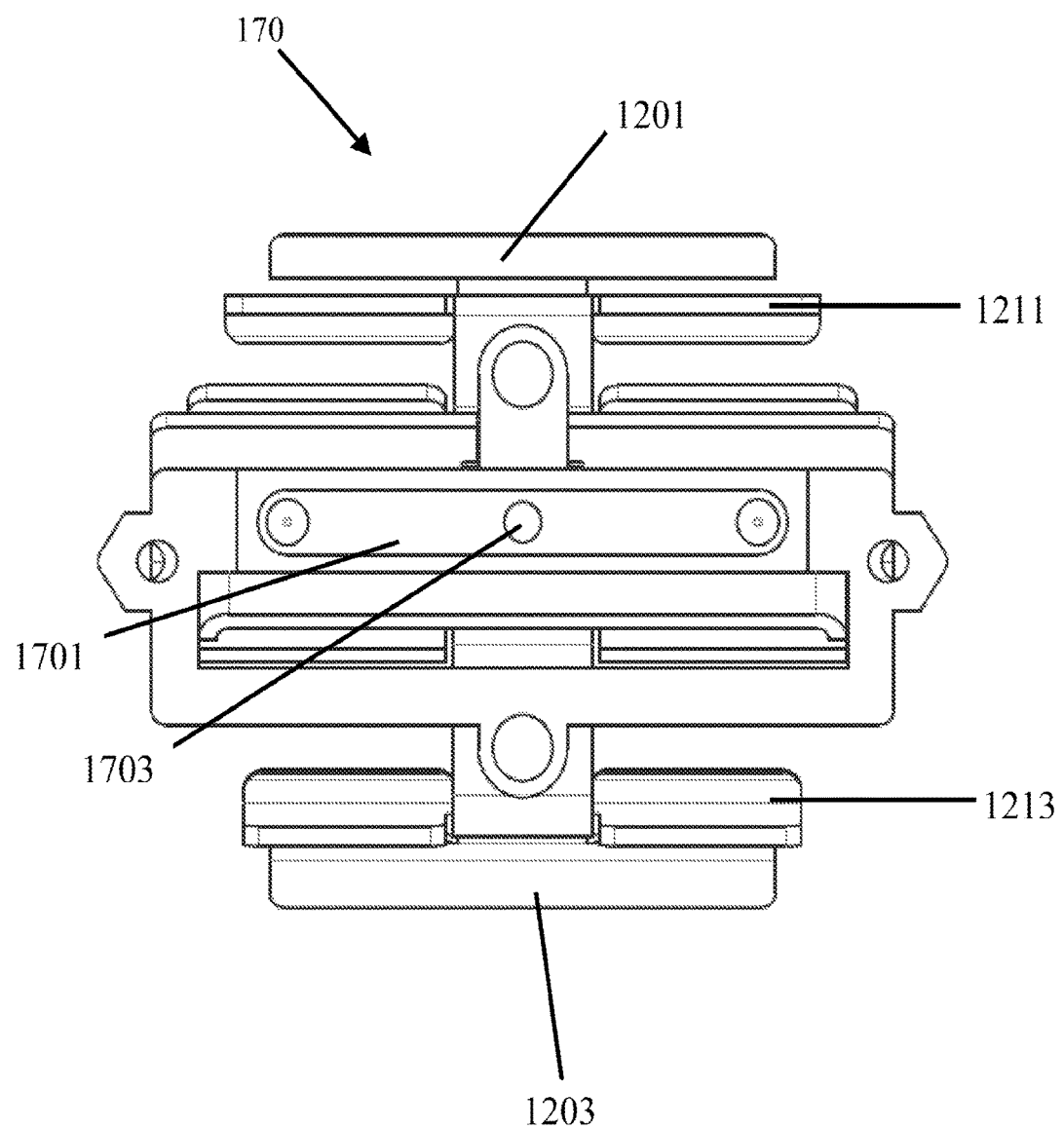
FIG. 18 shows a back view of the pivoting four-in-one cut guide of FIG. 17 with the pivoting pin plate in a horizontal position.
Figure 19:
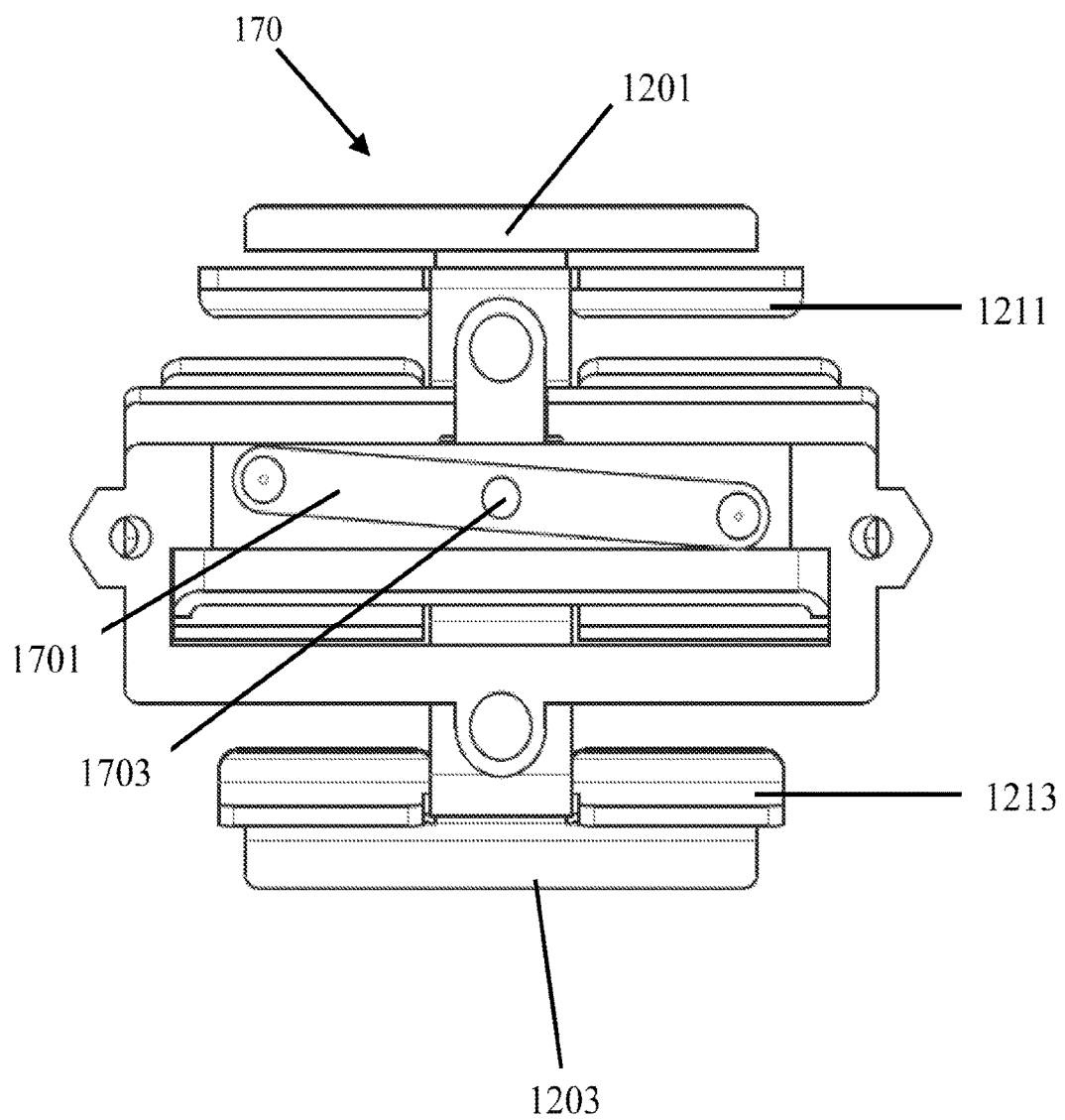
FIG. 19 shows a back view of the pivoting four-in-one cut guide of FIG. 17 with the pivoting pin plate in a rotated position.
Figure 20:
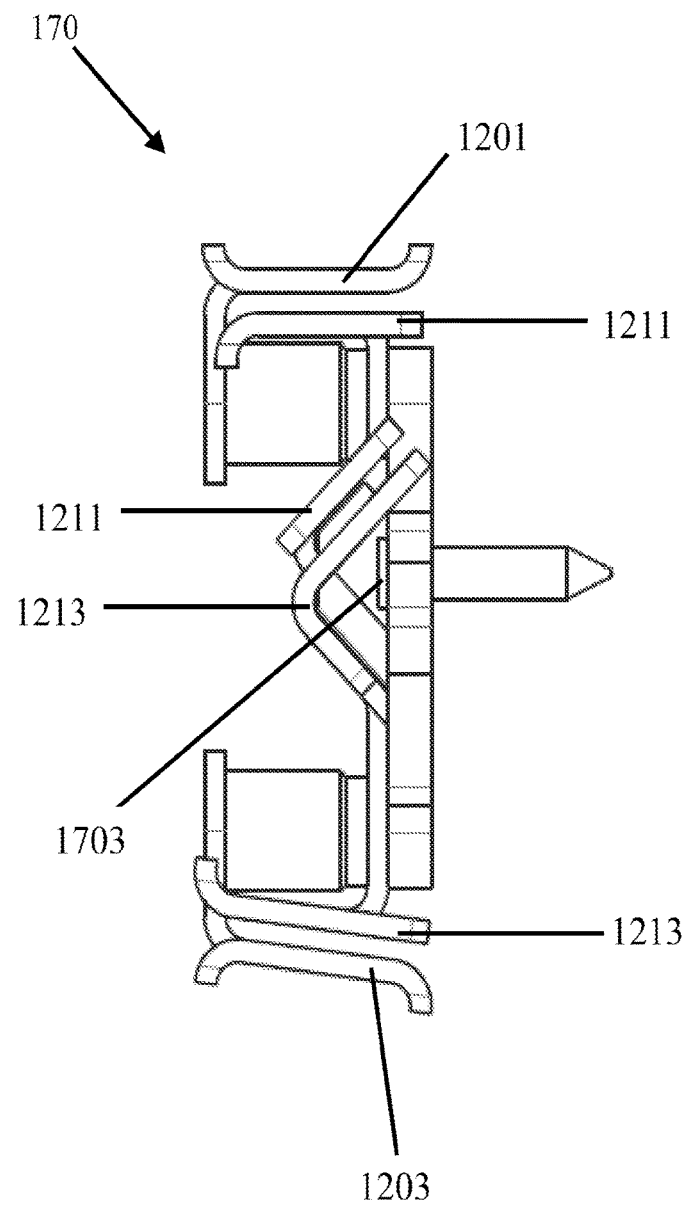
FIG. 20 shows a side view of the pivoting four-in-one cut guide of FIG. 17.

FIG. 17 shows an isometric view of pivoting four-in-one cut guide 170 with pivoting pin plate 1701 in its standard horizontal position attached via pivot point pin 1703. As previously stated, pivoting pin plate 1701 allows the surgeon to make slight changes to the axis orientation of pivoting four-in-one cut guide 170 by rotating the cut guide about the pivoting pin plate 1701 and pivot point pin 1703. FIG. 18 shows a bottom view of pivoting four-in-one cut guide 170 with pivoting pin plate 1701 in its horizontal position. FIG. 19 shows the same pivoting four-in-one cut guide with pivoting pin plate 1701 rotated out of its horizontal position, depicting its rotational ability. FIG. 20 shows a side view of the pivoting four-in-one cut guide 170 which clearly displays the location of pivot point pin 1703.

The configuration of the four-in-one cut guide 120 and the pivoting four-in-one cut guide 170 allows each of these devices to be manufactured from pieces of flat stock metal that are cut, bent into shape, and stacked on top of each other. In one embodiment, manufacturing the four-in-one cut guide 120 or the pivoting four-in-one cut guide 170 includes the following steps. First, a piece of flat stock stainless steel, or other suitable metal, is cut to create the exterior shape of one of the plates to be included in the device (e.g., the pin plate 1209, the anterior frame component 1211, the posterior frame component 1213, the anterior modular plate 1201, or the posterior modular plate 1203). The cutting operation may employ laser cutting, punching, die cutting, stamping or any other suitable method for cutting metal. Fastener holes may be cut into the plate at this stage, or later, after the bending operation discussed below. Upon completion of the cutting processes, the plate may be bent into a desired shape. For example, in the case of the posterior frame component 1213, the plate may be bent along a first bending line to create the mating male tab 1217 and a first cutting instrument guide surface that is angled relative to the bone engaging surface of the pin plate 1209, and bent along a second bending line to create a second angled cutting instrument guide surface corresponding to an end face of the posterior frame component 1213 to be positioned in opposition to the posterior modular plate 1203. Some or all of the edges of the plate may be bent to create stiffening ribs 1215. After the bending processes are complete, the plate may be heat treated to impart the plate with a desired hardness. Next, the plate may be subjected to a surface finishing operation such as tumbling and/or blasting. Additional pieces of flat stock metal may be processed according the foregoing steps to form the pin plate 1209, the anterior frame component 1211, the anterior modular plate 1201, and/or the posterior modular plate 1203. Next, the plates are stacked on top of each other and secured together by removably attaching the plates with mechanical fasteners (e.g., screw bosses 1205), welding the plates together to create a permanent attachment, and/or welding the plates together with a breakable, torque-until-failure member. Subsequently, the assembled four-in-one cut guide 120 or the pivoting four-in-one cut guide 170 may be cleaned, and finally, packaged in a sterile manner.

It will be appreciated by persons skilled in the art that numerous variations and/or modifications may be made to the described four-in-one cut guide 120 and pivoting four-in-one cut guide 170 and methods as specifically shown here without departing from the spirit or scope of that broader disclosure. The various examples are, therefore, to be considered in all respects as illustrative and not limiting.

Lastly described here are femoral trials that are far less expensive to manufacture than traditional femoral trials, while still mimicking the implanted femoral component and sustaining surgical needs in terms of assessment and confirmation of joint mechanics, range of motion, and soft tissue balance. Described is a better method of creating and supplying a strong and three-dimensionally accurate femoral trial in a much more cost effective method. Manufacturing techniques leverage laser cutting flat stock, flat stock that is bent into component(s), and component(s) that are assembled in order to create a sturdy three dimensional assembled composite. This assembly recreates important implant planes, simulating the five cuts of the femur: anterior, anterior chamfer, distal, posterior chamfer, and posterior. Two additional condylar struts providing both accurate geometric curvature at the center of each condyle, as well as two femoral lug drill bosses, are subsequently incorporated into the assembly. The three dimensional articulating surface is secondarily overmolded or subsequently stamped in a complex three dimensional dye, in order to create an accurate representation of the femoral implant articulating geometry. This unique method of creating a femoral trial utilizes one or more significantly cost effective manufacturing approaches.

Figure 21:
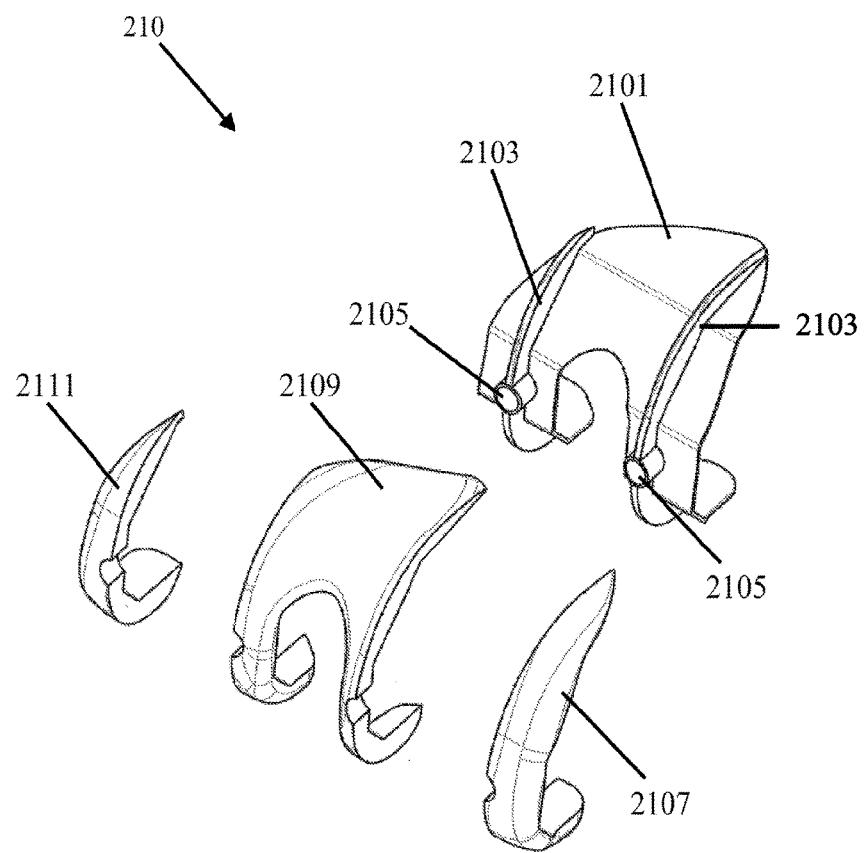
FIG. 21 shows an exploded view of the components of an overmolded femoral trial.

FIG. 21 shows an exploded view of the overmolded femoral trial 210 components. Stainless steel plate 2101 is the component in direct contact with the femur. On the anterior side of stainless steel plate 2101, the condylar struts 2103 and femoral lug drill bosses 2105 can be seen. Medial plastic overmolded articulating surface 2107, central plastic overmolded articulating surface 2109, and lateral plastic overmolded articulating surface 2111 are attached to the anterior surface of stainless steel plate 2101, surrounding the condylar struts 2103 and femoral lug drill bosses 2105.

Figure 22:
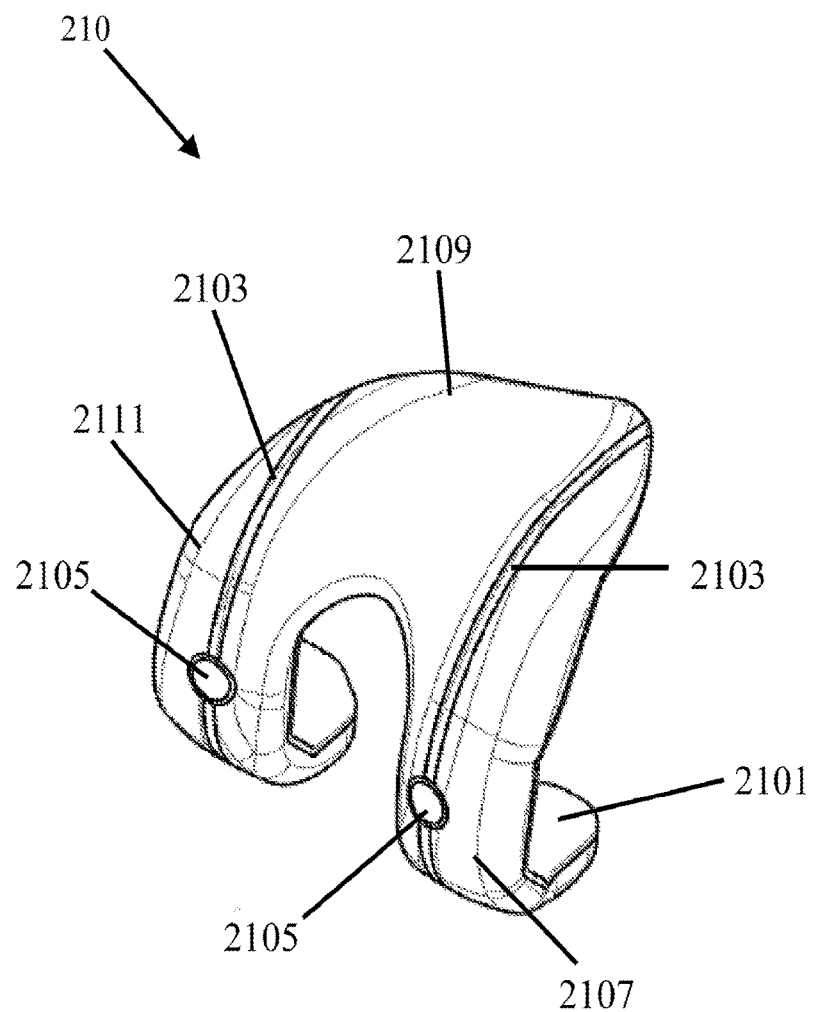
FIG. 22 shows an isometric view of the assembled overmolded femoral trial.

FIG. 22 shows an assembled view of the overmolded femoral trial 210. Condylar struts 2103, femoral lug drill bosses 2105, and medial overmolded articulating surface 2107, central overmolded articulating surface 2109, and lateral overmolded articulating surface 2111 can be seen in their respective final positions with respect to stainless steel plate 2101.

Figure 23:
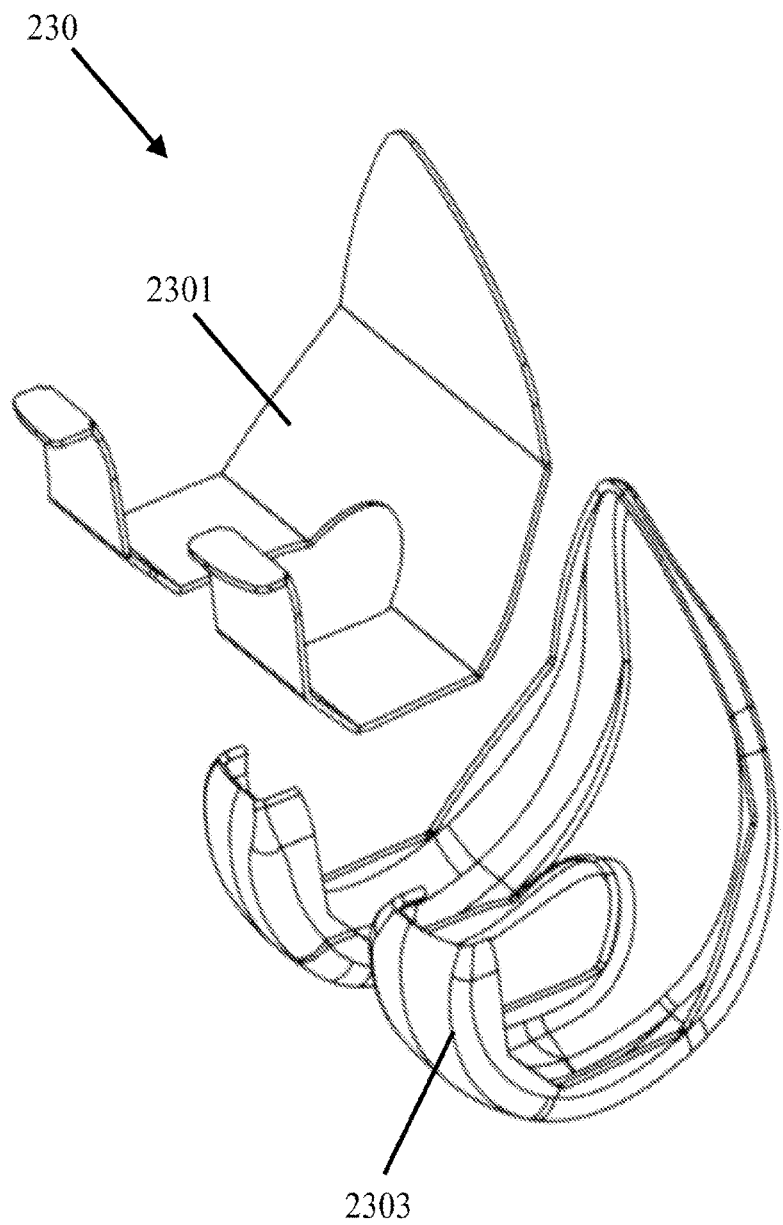
FIG. 23 shows an exploded view of the components of a stamped femoral trial.
Figure 24:
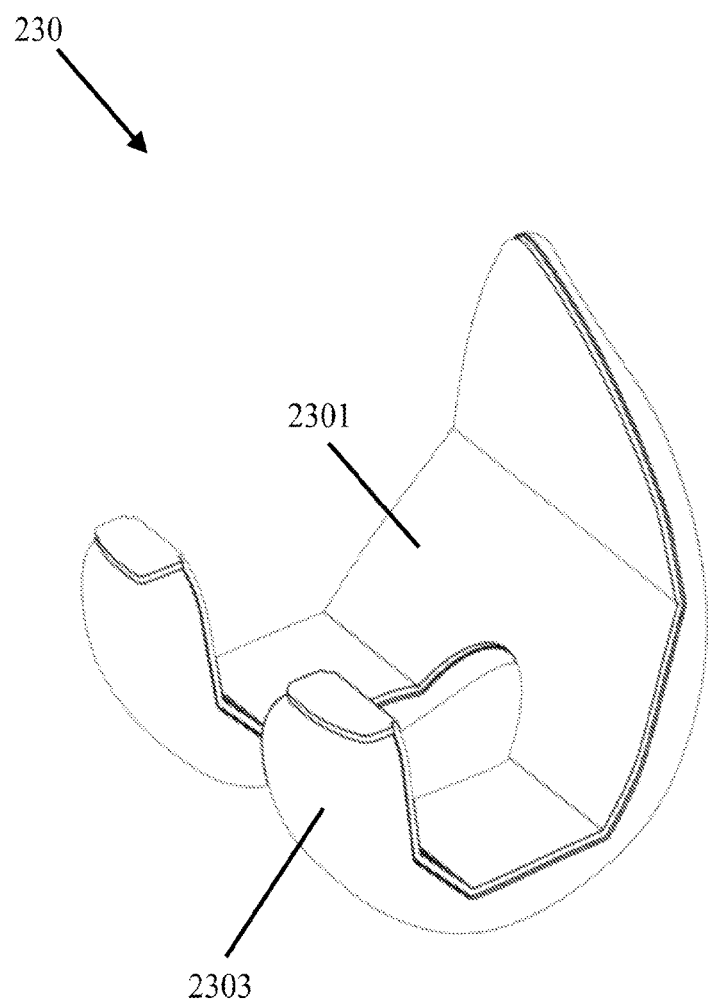
FIG. 24 shows an isometric view of the stamped femoral trial after assembly.
Figure 25:
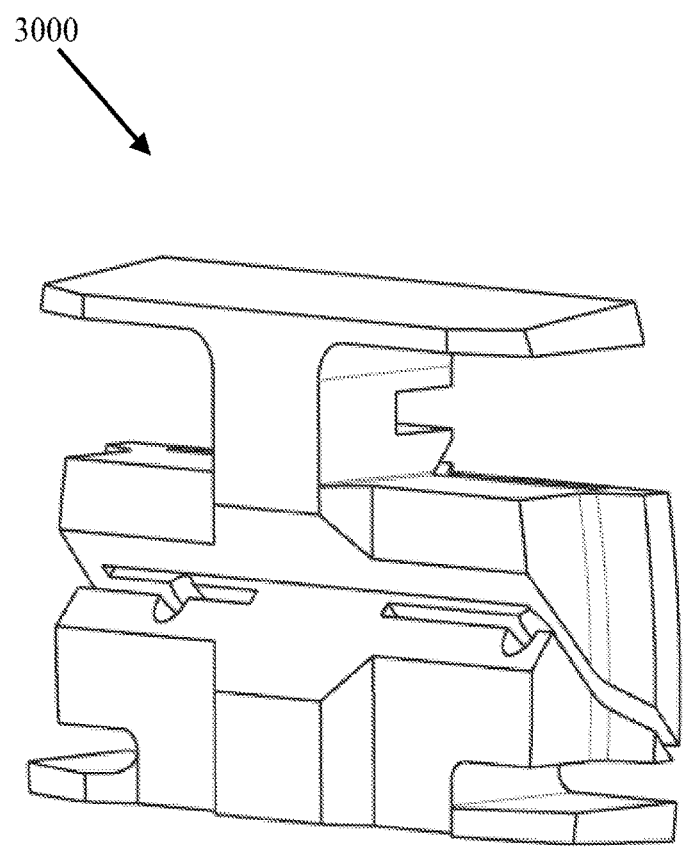
FIG. 25 is an isometric view of a traditional femoral cut guide.

Another unique method of producing the femoral trial employs a somewhat similar approach. FIG. 23 shows an exploded view of this stamped femoral trial 230. Stainless steel plate 2301 is the component in direct contact with the femur. Creating stainless steel plate 2301 would involve bending a singular piece of flat stock metal into the desired form. Then, single component articulating surface 2303 would be three dimensionally formed by being put through single or multiple stamping processes until the appropriate and desired surface is achieved. FIG. 24 shows an assembled view of stamped femoral trial 230 with components stainless steel plate 2301 and single component articulating surface 2303 in their respective final positions.

It will be appreciated by persons skilled in the art that numerous variations and/or modifications may be made to the overmolded femoral trial 210 and stamped femoral trial 230 and methods as specifically shown here without departing from the spirit or scope of that broader disclosure. The various examples are, therefore, to be considered in all respects as illustrative and not limiting.

While the foregoing embodiments of the surgical cutting guides and trials have been described primarily in connection with the preparation a femur bone during a surgical procedure, alternative embodiments of the surgical cutting guides and trials can be configured for the preparation of other anatomical features, including, for example, the shoulder, hip, ankle, neck, elbow, spine, ligaments, cartilage, and any other bone tissue.

What is claimed is:

1. A surgical cut guide comprising:
    a first end including a first bone tissue engaging surface and at least one bone tissue fastener hole extending through the first bone tissue engaging surface, the first bone tissue engaging surface being configured to engage bone tissue;
    a second end including second bone tissue engaging surface and at least one bone tissue fastener hole extending through the second bone tissue engaging surface, the second bone tissue engaging surface being angled relative to the first bone tissue engaging surface and configured to engage an anterior portion of the bone tissue;
    a body extending between and connecting the first end and the second end, the body including a third bone tissue engaging surface angled relative to the first bone tissue engaging surface and the second bone tissue engaging surface;
    a first projection defined by an interior portion of the body that bends away from the third bone tissue engaging surface, the first projection including a first guide surface angled relative to the third bone tissue engaging surface and defining a first guide path for guiding a cutting instrument;
    a second projection and a third projection defined by respective interior portions of the second end of the surgical cut guide that each bend away from the first bone tissue engaging surface, the second projection including a second guide surface angled relative to the first bone tissue engaging surface and defining a second guide path for guiding the cutting instrument, the third projection including a third guide surface angled relative to the first bone tissue engaging surface and defining a third guide path for guiding the cutting instrument, the second projection and the third projection being arranged such that the second guide surface faces the third guide surface and the second guide surface is parallel to the third guide surface.

2. The surgical cut guide of claim 1, the first projection including a rear surface parallel to the first guide surface.

3. The surgical cut guide of claim 1, the first projection terminating at a free end spaced apart from a remainder of the body.

* * * * *